(12) United States Patent
Stauffer et al.

(10) Patent No.: US 8,075,181 B1
(45) Date of Patent: Dec. 13, 2011

(54) THERMAL MONITORING DEVICE

(75) Inventors: Paul Rath Stauffer, Durham, NC (US); Celestino John Gaeta, Carlsbad, CA (US); Richard Alan Forber, Carlsbad, CA (US); Doug Peder Bonnell, Castle Rock, CO (US)

(73) Assignee: The Regents of the University of California, Oakland, CA (US)

( * ) Notice: Subject to any disclaimer, the term of this patent is extended or adjusted under 35 U.S.C. 154(b) by 376 days.

(21) Appl. No.: 12/475,151

(22) Filed: May 29, 2009

Related U.S. Application Data

(60) Provisional application No. 61/056,937, filed on May 29, 2008.

(51) Int. Cl.
  *G01K 3/00* (2006.01)
  *G01K 13/00* (2006.01)
  *G01J 5/00* (2006.01)
  *A61B 5/00* (2006.01)

(52) U.S. Cl. ............ 374/137; 374/121; 374/131; 600/2; 600/549; 607/101

(58) Field of Classification Search .................. 374/120, 374/121, 130, 131, 137, 161, 110; 607/101; 606/9, 27, 31, 33; 600/2, 474, 549
See application file for complete search history.

(56) References Cited

U.S. PATENT DOCUMENTS

| | | | | |
|---|---|---|---|---|
| 5,028,146 A | * | 7/1991 | Wada | 374/131 |
| 5,035,511 A | * | 7/1991 | Berthold | 374/124 |
| 6,330,479 B1 | | 12/2001 | Stauffer | |
| 7,582,050 B2 | * | 9/2009 | Schlorff et al. | 600/2 |
| 7,717,618 B2 | * | 5/2010 | Saxena et al. | 374/137 |
| 2005/0251235 A1 | | 11/2005 | Schlorff et al. | |

OTHER PUBLICATIONS

T. Juang et al., Construction of a Conformal Water Bolus Vest Applicator for Hyperthermia Treatment of Superficial Skin Cancer, Internat. Con. of the IEEE Eng. in Med. and Bio. Soc., Sep. 2004, pp. 1-4, San Francisco.
T. V. Samulski et al., Clinical Experience with a Multi-element Ultrasonic Hyperthermia System: Analysis of Treatment Temperatures, Internat. J. Hyperthermia, Sep. 1990, pp. 909-922, vol. 6, No. 5.
C. J. Diederich et al., Preclinical Evaluation of a Microwave Planar Array Applicator for Superficial Hyperthermia, Internat. J. Hyperthermia, Mar. 1993, pp. 227-246, vol. 9, No. 2.
C. J. Diederich et al., An Improved Bolus Configuration for Commercial Multielement Ultrasound and Microwave Hyperthermia Systems, Med. Phys., Jun. 1994, pp. 1401-1403, vol. 21, No. 9.
P. R. Stauffer et al., Preliminary Clinical Experience with Planar and Conformal Microwave Array Applicators for Hypothermia, Abstract of presentation given at 14th North American Hyperthermia Society Meeting, 1994, Nashville TN.
P. R. Stauffer, Thermal Therapy Techniques for Skin and Superficial Tissue Disease, Critical Review: Matching the Energy Source to the Clinical Need, Spie Optical Engineering Press, 2000, pp. 327-367.

(Continued)

*Primary Examiner* — Amy Cohen Johnson
(74) *Attorney, Agent, or Firm* — Burns & Levinson, LLP; Jacob N. Erlich, Esq.; David W. Gomes, Esq.

(57) ABSTRACT

A thermal monitoring sheet measures surface temperature distributions of large areas, even over large, contoured surfaces. The sheet incorporates conduits that terminate or intersect at temperature measurement locations with a fixed relative arrangement to form a two-dimensional grid for sensing temperature distributions.

22 Claims, 5 Drawing Sheets

OTHER PUBLICATIONS

P. R. Stauffer et al., Progress on System for Applying Simultaneous Heat and Brachytherapy to Large-area Surface Disease, Proc. of SPIE, 2005, pp. 82-96, vol. 5698.

T. Juang et al., Multilayer Conformal Applicator for Microwave Heating and Brachytherapy Treatment of Superficial Tissue Disease, Int. J. Hyperthermia, Nov. 2006, pp. 527-544.

P. R. Stauffer, Progress on Conformal Microwave Array Applicators for Heating Chestwall Disease, Proc. of SPIE, 2007, pp. 1-13, vol. 6440.

K. Arunachalam et al., Performance Evaluation of a Conformal Thermal Monitoring Sheet Sensor Array for Measurement of Surface Temperature Distributions During Superficial Hyperthermia Treatments, Int. J. Hyperthermia, 2008, pp. 313-325, vol. 24, No. 4.

K. Arunachalam et al., A Thermal Monitoring Sheet With Low Influence From Adjacent Waterbolus for Tissue Surface Thermometry During Clinical Hyperthermia, IEEE Trans. Biomed. Engr., Oct. 2008, pp. 2397-2406, vol. 55, No. 10.

P. R. Stauffer, Devices and Techniques for Thermal Therapy of Chest Wall Recurrence, Abstract of presentation for Society for Thermal Medicine 2006 Annual Meeting, 2006, Bethesda MD.

T. Juang et al., Improved Patient Interface for a Multilayer Conformal Applicator for Simultaneous Heat and Brachytherapy Treatment of Superficial Tissue Disease, Abstract of presentation for Society for Thermal Medicine 2006 Annual Meeting, 2006, Bethesda MD.

P. Stauffer et al., Progress on Conformal Microwave Array Applicators for Heating Large Area Chest Wall Disease, Abstract of presentation for Euro. Soc. for Hyperthermic Oncology 24th Annual Meeting, Jun. 2007, Prague.

K. Arunachalam et al, Characterization of Surface Thermometry Approaches for Clinical Hyperthermia, Abstract of presentation for 10th Int. Congress on Hyperthermic Oncology, Apr. 2008, Munich.

Michael M. Salour, U.S. Appl. No. 12/475,044, filed May 29, 2009, titled Imaging Temperature Sensing System.

Celestino J. Gaeta, U.S. Appl. No. 12/429,463, filed Apr. 24, 2009, titled Passive Wavelength-Division Multiplexing (WDM) Fiber-Optic Temperature Sensor.

Michael M. Salour, U.S. Appl. No. 12/468,598, filed May 19, 2009, titled Multiple Sensing Tip Optical Fiber Thermometer.

* cited by examiner

THERMAL MONITORING DEVICE

CROSS REFERENCE TO RELATED APPLICATIONS

This application claims priority of provisional application Ser. No. 61/056,937 filed May 29, 2008 entitled THERMAL MONITORING SHEET and which provisional application is incorporated herein in its entirety.

STATEMENT REGARDING FEDERALLY SPONSORED RESEARCH OR DEVELOPMENT

This invention was made with government support under Contract No. NIH 1R43-AR051278-01 awarded by the National Institute of Health. The government has certain rights in the invention.

BACKGROUND

For therapeutic use of heat in cancer therapy, it is critically important to monitor and control tissue temperature within a narrow window (~40-45° C.) to ensure adequate therapy without complications. Hyperthermia clinics including, but not limited to, University of California San Francisco (UCSF) operate equipment such as, but not limited to, a Sonotherm 1000 (Labthermics Technologies, Champaign Ill.) 16 transducer 4×4 planar array 3.4 MHz ultrasound heating device and a Microtherm 1000 (Labthermics Technologies, Champaign Ill.) 16 antenna 4×4 planar array 915 MHz microwave heating device for applications such as, but not limited to, treating superficial tissue regions up to 15×15 cm square and as much as 4 cm deep (ultrasound) or 1.5 cm deep (microwave) below the skin.

Recently a 32 channel 915 MHz Conformal Microwave Array hyperthermia system has been approved for use in the patient clinic at University of California San Francisco and use on the first 14 patients demonstrated the ability to deliver highly adjustable heating patterns to much larger surface areas than ever before, even when the disease is spread across contoured portions of the anatomy such as the human torso.

The common problem in administering treatments with multi-element array-heating devices is gaining sufficient feedback about the tissue temperature under each independently powered heat source. The planar array microwave applicator comes with a small number of fiber-optic sensors, often less than the number of power sources, which are placed at a small number of points under the multi-element array applicator to sample the tissue temperature distribution. This small sampling of temperature is inadequate for real-time feedback control of multiple power amplifiers. For a better assessment of temperature distribution under such heating arrays, sensors may be pulled manually within special thermal mapping catheters lying on the tissue surface and temperatures recorded at 5-10 mm spaced positions across the surface. This thermal mapping procedure significantly increases the number of surface temperature measurements by providing one or more linear profiles of surface temperature under the heating array, but is tedious and time consuming to generate, and does not provide a true two dimensional characterization of surface temperature distribution.

SUMMARY

The needs for the invention set forth above as well as further and other needs and advantages of the present invention are achieved by the embodiments of the invention described herein below.

Various embodiments of this invention relate generally to measurement of two-dimensional temperature distributions. Numerous applications exist in, but are not limited to, laboratory, industrial, and clinical environments that can benefit from improved accuracy and simplicity of monitoring complete surface temperature distributions with a single convenient device. One medical application, but not limited to, is the monitoring and control of hyperthermia therapy for superficial tissue disease such as chest wall recurrence of breast cancer or plaque psoriasis. This type of therapy is conducted via heat treatment from multi-element array microwave or ultrasound hyperthermia applicators that spread heat as uniformly as possible over a contoured surface of the human body.

The limitations of past temperature monitoring approaches are overcome with a pre-configured thermal monitoring sheet (TMS) with appropriately spaced array of non-perturbing optical waveguide sensors that speed up and simplify critically important thermal monitoring procedures and allow continuous thermal feedback for possible use in automatic control that may be associated with such procedures including, but not limited to, control of power to multiple element heat applicators.

The thermal monitoring sheet should facilitate clinical temperature monitoring of large contoured surfaces. Fast and accurate characterization of temperature distributions coupled with automated feedback power control should provide significantly improved heating patterns from existing clinical hyperthermia applicators as well as encourage the design of new superficial hyperthermia applicators with increasing levels of adjustability to fit the complex curvature of the human torso.

Monitoring of the unknown skin surface temperature at an interface with a plastic membrane-encased waterbolus at another temperature is difficult. Existing techniques for monitoring surface temperature include single-sensor or multiple-sensor plastic-encased thermocouples, high resistance lead thermistors, and fiber-optic sensors. A plastic coating is required to make the sensors reusable (durable and cleanable), but serves as an insulating layer that impacts the temperature measurement result. Thermal mapping techniques have been used to increase the number of measured points by pulling individual sensors through catheters on the skin surface. Addition of a plastic catheter with larger diameter than the sensor in order to facilitate mapping adds uncertainty and time delay to the readings however, due to air around the sensor and asymetric contact of the smaller sensor to the inside wall of the round catheter. Thus the typically used round sensor cross-section and multiple layers of plastic and air insulation increase the uncertainty of skin surface measurements, particularly at the interface between two dissimilar materials (i.e. PVC encased waterbolus and tissue). With a present embodiment, a planar sheet of predetermined construction, employing regularly spaced arrays of stationary fiber-optic temperature sensors incorporating a series of removable connectors to access electronics and display components offers significantly improved measurement of the interface temperature.

Another embodiment includes a thermal monitoring device having a first plurality of conduits for conveying electromagnetic radiation in a first predetermined direction, a second plurality of conduits for conveying electromagnetic radiation in a second predetermined direction, the second plurality of conduits intersecting the first plurality of conduits at a plurality of intersecting positions; a plurality of temperature sensing components, with a separate temperature sensing component located at each of the intersecting positions; a flexible component maintaining the first and the second plurality of conduits in a fixed relative arrangement with respect to each other; each of the first plurality of conduits having a portion that terminates in a first connector; and each of the second plurality of conduits having a portion that terminates in a second connector; wherein electromagnetic radiation can be input through the first connector via the first plurality of conduits to each the temperature sensing component, each temperature sensing component providing an output through the second connector indicative of temperature substantially at the temperature sensing component.

Potential applications of the invention, but not limited thereto include, for example:

surface-temperature monitoring of skin or sub-surface tissue disease, with or without concurrent microwave or ultrasound heat treatment;

temperature measurement component of automatic feedback control circuit used to regulate power of multiple element heat applicators;

recording 2D temperature distributions of large flat or contoured surfaces, which may be either open to air or buried inside layered media;

industrial process monitoring which, might include surface temperature monitoring of large flat or contoured metal, plastic or other constituent surfaces as in monitoring temperature of machinery parts to ensure they do not get too hot during a machining process, monitoring surface temperature distribution of the sidewall of a large mixing vessel for instance to monitor progress or completion of an exothermic reaction while mixing multiple component chemicals;

monitoring temperature distribution of an interface between two dissimilar materials or between layers of similar materials (solid or liquid) during heating or cooling to monitor temperature uniformity or for control feedback to obtain a desired non-uniform temperature, although clinical hyperthermia monitoring applications have been highlighted here, this surface-monitoring device may be useful for numerous general laboratory applications in addition to clinical thermometry. For a better understanding of the present invention, together with other and further needs thereof, reference is made to the accompanying drawings and detailed description and its scope will be pointed out in the appended claims.

DETAILED DESCRIPTION

Figure 1:
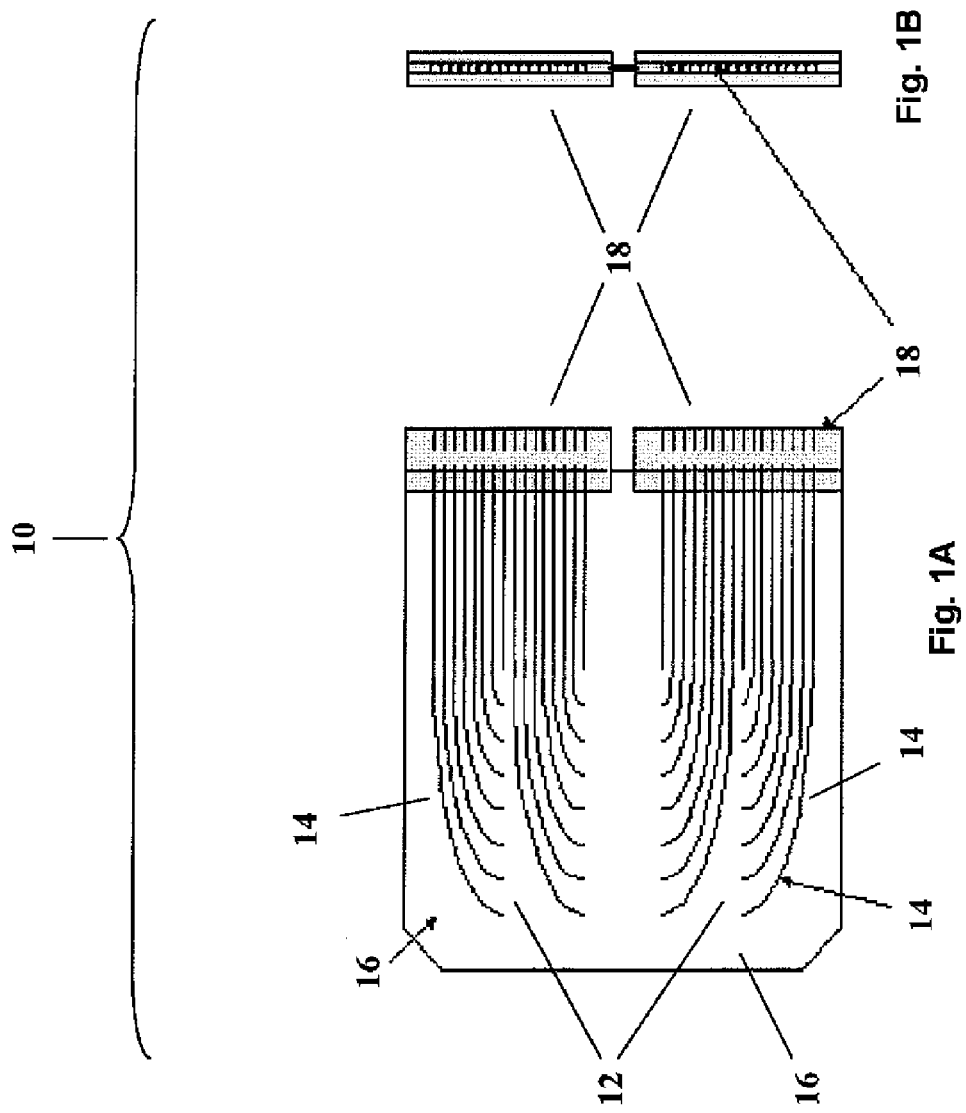
FIG. 1A is a schematic block diagram illustration featuring top view of a dielectric sheet TMS with an imbedded fiber-optic sensor array and low-profile multi-element connectors.
FIG. 1B is a schematic block diagram illustration featuring side view of a dielectric sheet TMS shown in FIG. 1A.

An embodiment of the thermal monitoring sheet (TMS) includes, but is not limited to, a number of temperature sensing elements (nodes) arranged to form a two dimensional array with fixed relative spacing between the points of measurement. The temperature sensing nodes may be accessed optically, especially in the case of optical temperature sensors including, but not limited to, fluorescence-decay temperature sensors. Cabling such as, but not limited to, fiber optic cable may be employed to interface between the TMS and readout electronics.

One embodiment is shown in FIGS. 1A and 1B, for the case of, for example, but not limited to, a 32-element TMS sensor array 10, as shown in FIG. 1A, where temperature-sensing nodes 12 at the ends of conduits 14 such as, but not limited to, optical waveguides are arranged with a fixed relative spacing that is captured or formed, on or within a sheet material 16 exhibiting high thermal conductivity such as, but not limited to, Kapton material to form the thermal monitoring sheet. The other end of each of the conduits 14 is terminated in a connector 18. For most applications, the sheet material 16 should have a high thermal conductivity and be flexible to conform to the surface being monitored. The connector 18 shown in FIGS. 1A and 1B could be a passive connector but could also contain devices for operating the temperature-sensing nodes 12.

In applications where microwave, ultrasonic, or other radiation is to be passed through the TMS array, the physical parameters of the array should be selected to minimize any perturbations of the transmitted energy (especially perturbations leading to spatial non-uniformities in the radiation pattern). Many, but not all, embodiments for these applications would employ either fiber-optic or integrated-optical waveguide formats for the conduits 14. Some techniques for implementing the embodiment shown in FIGS. 1A and 1B include, but are not limited to, the following:

Rectangular or other shape single sheet of dielectric (i.e. such as, but not limited to, Kapton, Polyimide, liquid crystal polymer (LCP), polyurethane, polyethylene, PVC, etc) with temperature sensors and conduits attached by, for example, but not limited to, gluing to one surface in a regularly spaced 2D array, with included optical connectors for interfacing with separate external cabling.

The TMS is made up of at least two layers of rectangular or other shape dielectric glued or otherwise held together as a sandwich with temperature sensors and conduits trapped in a regularly spaced 2D array between or within the layers, with included optical connectors for interfacing with separate external cabling.

Temperature sensors referenced above may be constructed from, but are not limited to, optical fiber coupled temperature sensitive material, high-resistance lead (e.g. carbon fiber)

coupled thermistors, metal wire-coupled thermocouple junctions, or metal wire-coupled thermistors, or the like.

At least two layers of rectangular or other shape dielectric material can be identical to provide equal temperature sensitivity to surfaces in contact with the TMS array, or directional sensing of one surface relative to other surfaces may be provided using at least one layer with higher thermal resistance and at least one layer with lower thermal resistance on either side of the embedded temperature sensors.

A single layer sheet or double layer sandwich sensor array may be formed as the front skin-contacting surface of a closed flexible compartment containing temperature controlled liquid (e.g. water or oil) for coupling electromagnetic or ultrasonic energy into tissue.

Figure 2:
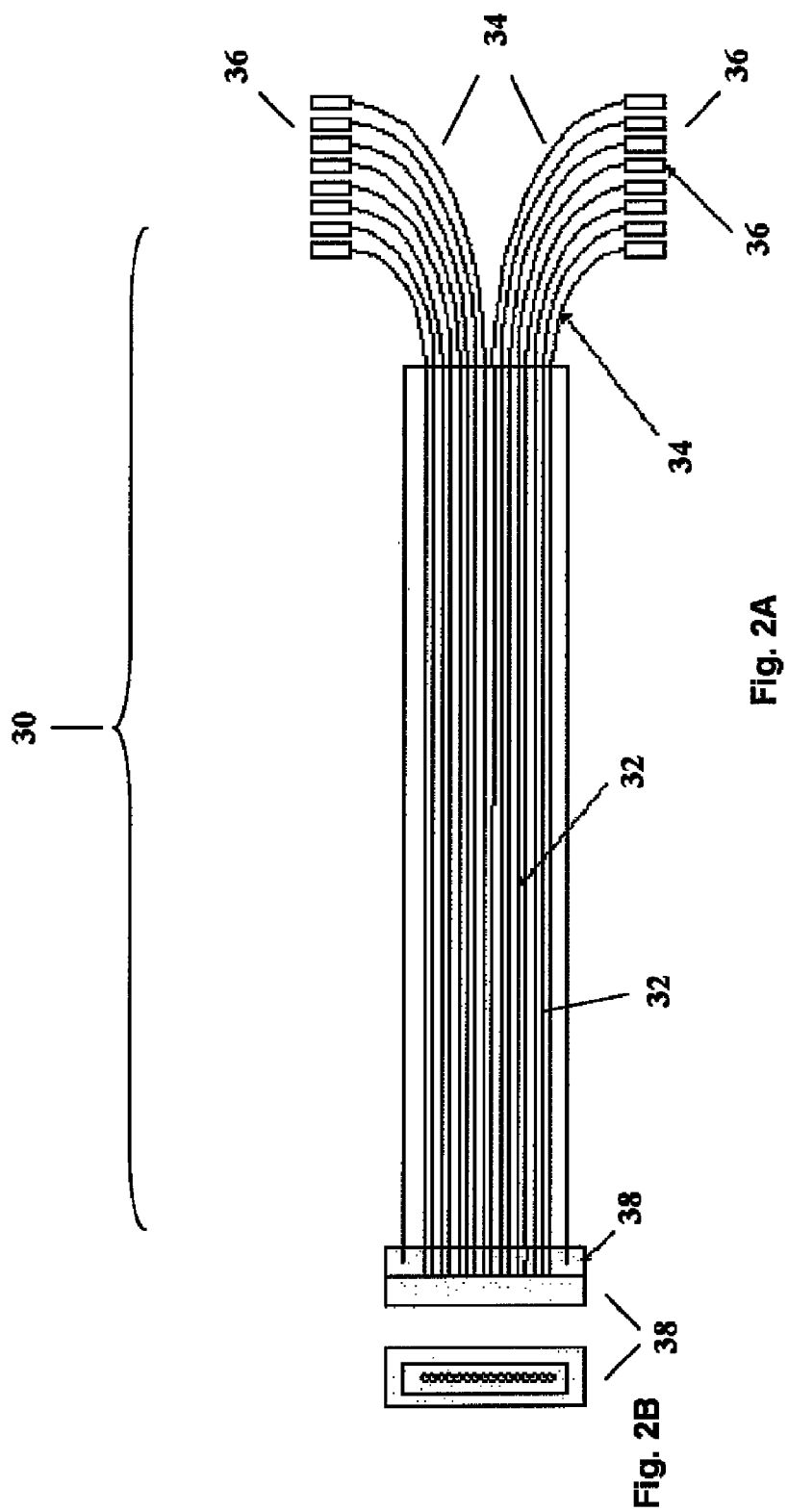
FIG. 2A is a schematic block diagram illustration with top view of a ribbon-format optical cable and low-profile multi-channel connector for use with the TMS incorporating an imbedded fiber-optic sensor array.
FIG. 2B is a schematic block diagram illustration with side view of a ribbon-format optical cable and low-profile multi-channel connector shown in FIG. 2A.

FIGS. 2A and 2B show a schematic embodiment of an embodiment of an interface cable 30 (shown in FIG. 2A) suitable for, but not limited to being used for, the TMS embodiment of FIG. 1. A ribbon cable 32 is made up of, but not limited to, conduits 34 such as, but not limited to, optical fibers that are individually terminated at connectors 36 on one end and terminated at a common connector 38, shown in FIGS. 2A and 2B, on the other end.

Figure 3:
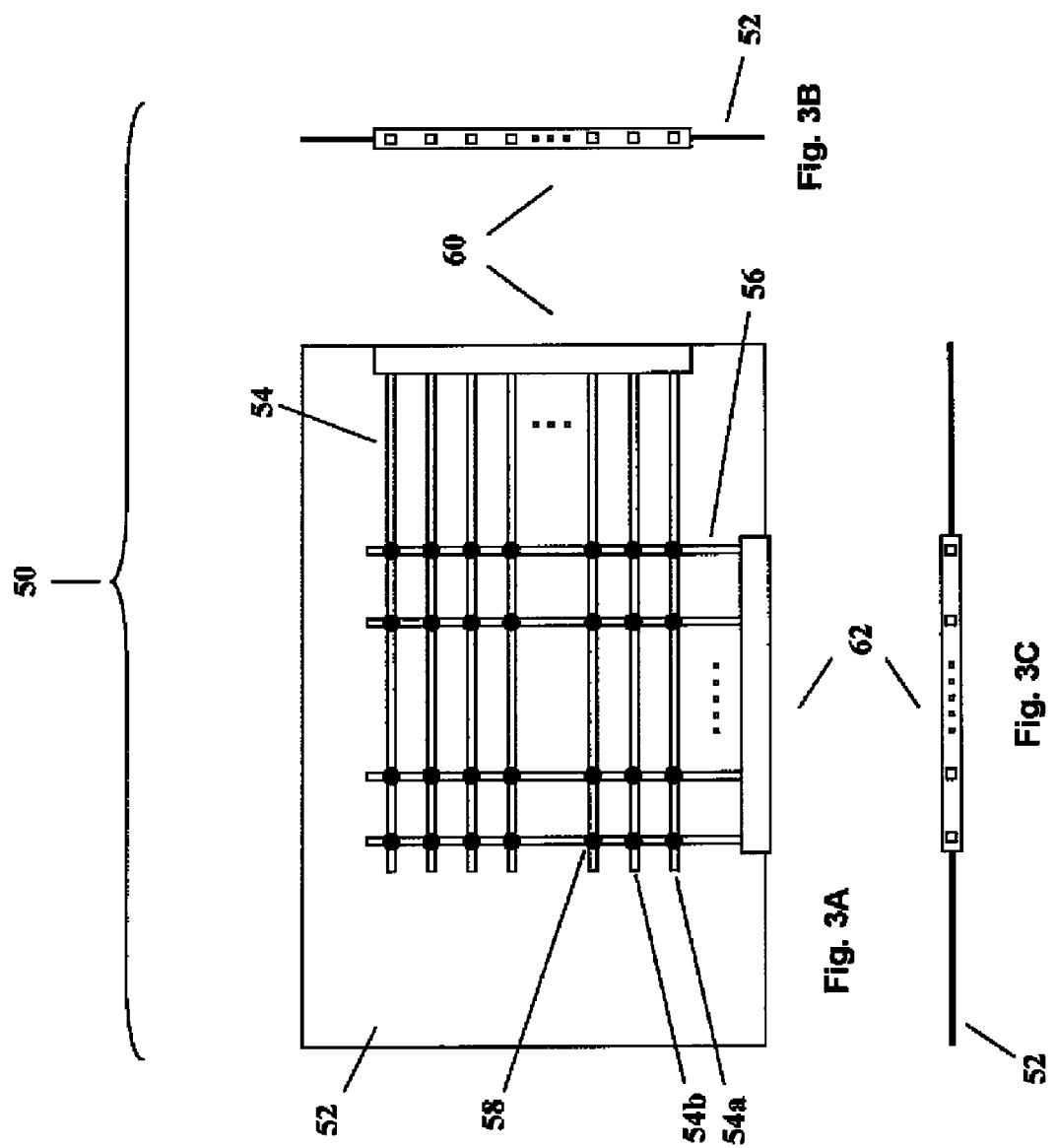
FIG. 3A is a schematic block diagram illustration featuring top view of another embodiment of a dielectric sheet TMS with an integrated optical waveguide sensor array and low-profile multi-element connectors.
FIG. 3B is a schematic block diagram illustration featuring a side view of the dielectric sheet TMS as shown in FIG. 3A.
FIG. 3C is a schematic block diagram illustration featuring another side view of a dielectric sheet TMS as shown in FIG. 3A.

Another embodiment of a TMS (50) is shown schematically in FIGS. 3A, 3B, and 3C. As shown in FIG. 3A, sheet 52 (also shown in FIGS. 3B and 3C) of material including, but not limited to, dielectric material with overlapping sets 54 and 56 of conduits such as, but not limited to, optical waveguides formed near, or at, a surface of the sheet using technologies such as, but not limited to, photo-masks, photoresist, ion-diffusion, laser etching, and photo-bleaching where one set of conduits 54 of the overlapping sets 54 and 56 of conduits is oriented generally in one direction and the other set of conduits 56 of the overlapping sets 54 and 56 of conduits are oriented generally in another direction yielding a relative orientation between the overlapping sets 54 and 56 of conduits including, but not limited to, an orthogonal relative orientation. A sensing temperature component 58 such as, but not limited to, a phosphor exhibiting temperature-dependent fluorescence decay, is located at each of the intersections of the overlapping sets 54 and 56 of conduits. Connectors 60 (shown in FIGS. 3A and 3B) and 62 (shown in FIGS. 3A and 3C) provide an interface to the overlapping sets 54 and 56, respectively, of conduits. Either or both of the connectors 60 and 62 could be a passive connector but could also contain devices for operating the sensing temperature components 58 located at the intersections of overlapping sets 54 and 56. Such devices include, but are not limited to, laser diodes, light emitting diodes (LED), optical detectors, infrared devices, and wireless devices. The connectors 60 and 62 could also be, but are not limited to being, detachable allowing for a disposable sheet 52 with reusable connectors 60 and 62.

Examples of the TMS 50 include, but are not limited to, a single sheet of dielectric with surface waveguides, two sheets of dielectric with waveguides oriented parallel to each other in each sheet and the sheets rotated relative to each other and laser active ions diffused into the points of intersection between the two sandwiched sheets.

A method of use for the TMS 50 includes, but is not limited to, utilizing one conduit, for example, but not limited to, conduit 54a of the set of conduits 54 in a given period of time to activate only the temperature sensing components 58 located on the one conduit (for example, conduit 54a) substantially during that time period. The activation signal is received via the connector 60 and transmitted through the one conduit (for example, conduit 54a). In response to the activation, the activated temperature sensing components 58 output readout signals related to the temperatures being measured by the activated temperature sensing components 58. The readout signals are conveyed substantially simultaneously by the set of conduits 56 to connector 62 for output from the TMS 50.

Another period of time may involve a different one conduit, for example, but not limited to, conduit 54b of the set of conduits 54. Only the temperature sensing components 58 located on the one conduit (for example, conduit 54b) are activated substantially during that time. The activation signal is received in the one conduit (for example, conduit 54b) via the connector 60, for example. In response to the activation, the activated temperature sensing components 58 output readout signals related to the temperatures being measured by the activated temperature sensing components 58. The readout signals are conveyed substantially simultaneously by the set of conduits 56 to connector 62 for output from the TMS 50. This activation and readout procedure may be continued until all of the conduits of the set of conduits 54 have been used for activation, for example, one conduit at a time, so that, for example, all temperature-sensing components in the TMS 50 have been activated. The entire procedure may be repeated to provide on-going monitoring of temperature.

The embodiment and process described allows for a large number of temperature measurement points with minimal conduits. Present temperature measurement systems require one conduit for each measurement point. In contrast, the embodiments of this invention allow for the number of temperature measurement points to be substantially equal to the product of the number of conduits 54 and the number of conduits 56 of the overlapping sets 54 and 56 of conduits. For example, the total number of conduits, given the sum of the number of conduits in the sets of conduits 54 and conduits 56, is substantially less than the number of temperature sensing components 58 (measurement points) that is given by the product of the number of conduits in the sets of conduits 54 and conduits 56. This advantage greatly simplifies the sensor system design, and makes it possible to achieve a large number of temperature measurement points.

Figure 4:
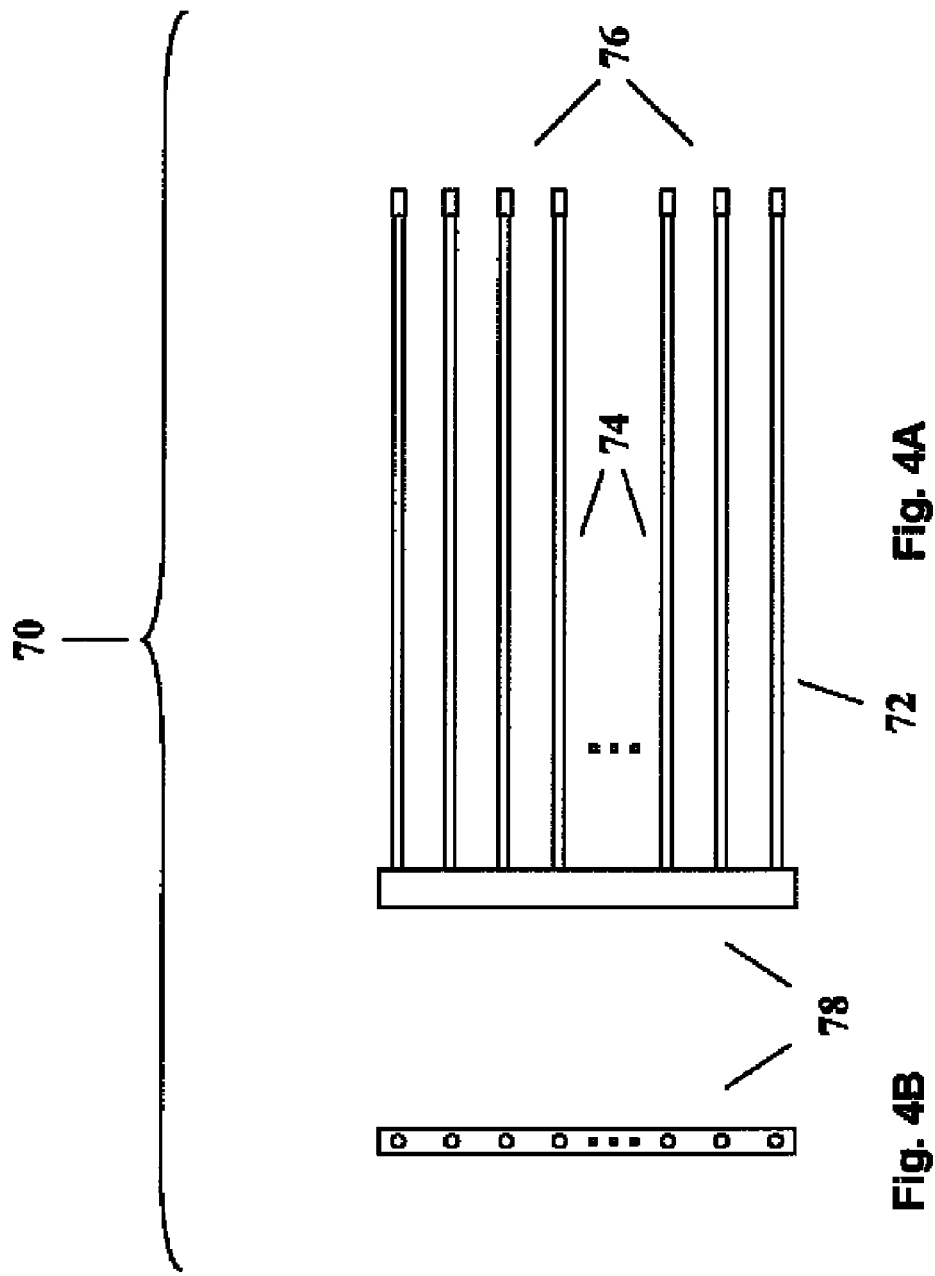
FIG. 4A is a schematic block diagram illustration with top view of another embodiment ribbon-format optical cable for use with the TMS incorporating an integrated optical waveguide sensor array.
FIG. 4B is a schematic block diagram illustration with side view of a ribbon-format optical cable as shown in FIG. 4A.

FIGS. 4A and 4B show a schematic embodiment of an interface cable 70 suitable for, but not limited to being used for, the TMS embodiment of FIG. 3A. As shown in FIG. 4A, a ribbon cable 72 consists of conduits 74 such as, but not limited to, optical fibers that are individually terminated at connectors 76 on one end and terminated at a common connector 78 (shown in FIGS. 4A and 4B) on the other end.

Figure 5:
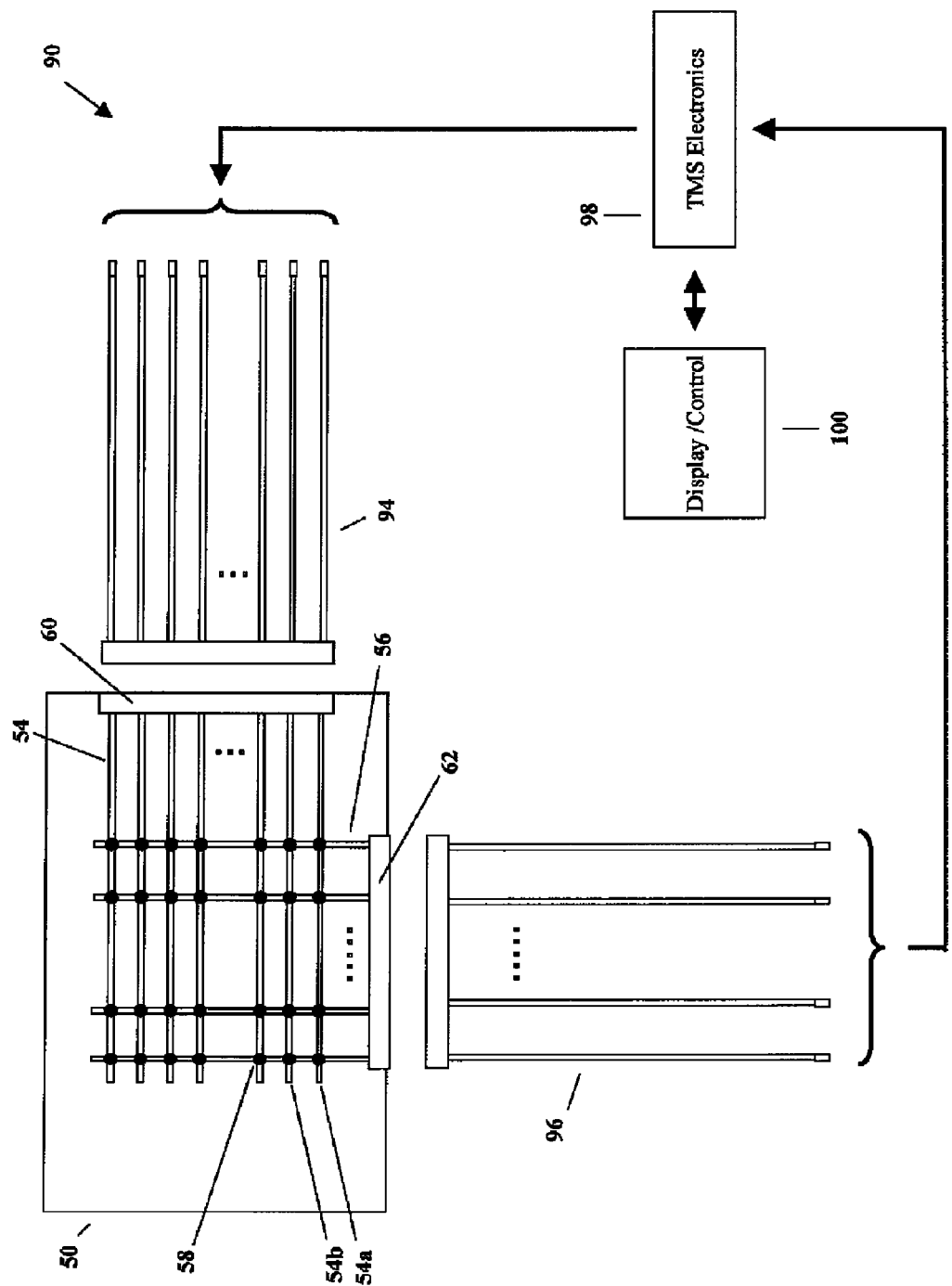
FIG. 5 is a schematic block system diagram for the TMS incorporating an integrated optical waveguide sensor array.

A TMS system embodiment 90 is shown in FIG. 5 utilizing a TMS 92 (50) and interface cables 94 (70) and 96 (70), as well as TMS electronics 98 and a display/control interface 100.

One implementation of the TMS system embodiment 90 may be implemented with, but is not limited to, the TMS 50 in which the set of conduits 54 and 56, comprise, but are not limited to, optical waveguides. The TMS electronics 98 may contain a source of electromagnetic radiation, for example, but not limited to, a laser-diode or LED for activating temperature sensing components 58. The excitation (activation) light propagates in the interface cable 94, comprising, for example, but not limited to, a fiber-optic cable assembly. The excitation light from the interface cable 94 enters the conduits 54 via the connector 60, and subsequently propagates in the conduits 54 to the temperature sensing components 58. The temperature sensing components 58 comprise, for example, but are not limited to, phosphors exhibiting temperature-dependent fluorescence decay. The set of conduits 56 comprise, for example, but are not limited to, optical waveguides delivering read-out light from the temperature sensing components 58 to the TMS electronics 98 via the connector 62, and the interface cable 96, comprising, for example, but not limited to, a fiber-optic cable assembly. In one mode of operation, for example, the TMS electronics 98 could provide light in only one conduit, for example, but not limited to, conduit 54a, of the set of conduits 54 during one period of time to activate only the temperature sensing components 58 that are located on the one conduit (for example, conduit 54a) substantially during that time period. In response to the activation, the activated temperature sensing components 58 output readout signals related to the temperatures being measured by the activated temperature sensing components 58. The readout signals are conveyed substantially simultaneously by the set of conduits 56 to connector 62, subsequently enter the interface cable 96, and propagate in the interface cable 96 to the TMS electronics 98 to provide a temperature readout on display control 100 based on the temperature at selected temperature sensing components 58. The decay, for example, but not limited to, of the phosphor of temperature sensing component 58 provides information relating to the temperature at that site.

Another period of time may involve a different one conduit, for example, but not limited to, conduit 54b of the set of conduits 54. Only the temperature sensing components 58 located on the one conduit (for example, conduit 54b) are activated substantially during that period of time. In response to the activation, the activated temperature sensing components 58 output readout signals related to the temperatures being measured by the activated temperature sensing components 58. The readout signals are conveyed substantially simultaneously by the set of conduits 56 to connector 62, subsequently enter the interface cable 96, and propagate in the interface cable 96 to the TMS electronics 98. This activation and readout procedure may be continued until all of the conduits of the set of conduits 54 have been used for activation, for example, one conduit of the set of conduits 54 at a time, so that, for example, all temperature-sensing components in the TMS 50 have been activated. The entire procedure may be repeated to provide on-going monitoring of temperature.

One use of the TMS may be in the form of a medical application, but is not limited thereto, monitoring temperatures at various locations on the skin surface of a patient undergoing hyperthermia treatment for large-area skin disease such as, but not limited to, chestwall recurrence of breast cancer. In this example, a two-dimensional array of microwave applicators provides heat to kill skin cancer cells over a wide area of the chest wall, usually in combination with radiation and/or chemotherapy. The TMS system embodiment of FIG. 5 provides feedback of temperature data over the surface subjected to the microwave radiation so as to facilitate monitoring and control of thermal dosage.

It should be further realized that the thermal monitoring sheets described herein may be constructed, but are not limited to the concepts described below. For this purpose, standard commercial fiber-optic (single-point) temperature sensors conform to a two-dimensional array format. Plastic fiber used in the sensors is cut to form array segments of staggered length. A temperature-sensitive phosphor or the equivalent is then added at the sensing end of each segment, and the segments arranged so the sensing tips are located in a uniformly spaced 4×4 array with adjacent tips separated by 3.7 centimeters. The fiber array is embedded between two Kapton sheets to form a thermal monitoring sheet with a fixed-position array of temperature sensors. One embodiment of the array can be constructed using approximately 250 μm diameter fibers, although not limited thereto.

Each fiber of the thermal monitoring sheet may be individually terminated in an optical connector so that it could be accessed by commercial signal-conditioner readout electronics. A furcation tube, incorporating Kevlar (or similar material) reinforcement, protects the fiber extending from the connector over most of its length. The outer diameter of the furcation tubing may be 2 mm for a 250 μm fiber. This furcation tubing extends about 3 m, making the complete assembly about 3.4 meters in length. Near the thermal monitoring sheet, the furcation tubing is terminated with a section of transition tubing. The outer diameter of the transition tubing is 800 μm for 250 μm fibers, for example. The fiber extends past the end of the transition tubing so that a short length of exposed 250 μm fiber traverses the region of the sensing array.

The exposed sections of optical fiber protruding from the transition tubing are sandwiched between two layers of thin and flexible Kapton that are held together with adhesive. In one embodiment, the two layers of Kapton are identical to allow equal sensing of temperature on both sides of the sheet. In another embodiment, two different thickness layers are used to provide directional thermal sensitivity of the buried fiber optic sensor (one layer of Kapton, for example, is approximately 100 μm in thickness while the other is approximately 175 μm thick). The Kapton material is cut in a rectangular shape, for example, around the 4×4 sensor array sandwich. The Kapton sandwich captures approximately 5 cm of the transition tubing, adding strength to the probe/sheet junction. A 10 cm length of transition tubing is reinforced as it exits the sheet to further strengthen this stress point on the fibers. It should be realized that the dimensions are for example only and not to limit the present embodiments.

Each of the, for example, 16 sensors comprising the TMS array may be individually connected to conventional signal-conditioner readout electronics (not shown). Temperatures may be displayed in both graphical and digital format on a computer monitor. The sensor responses may be measured against a NIST traceable standard RTD after placing the thermal monitoring sheet into an oil bath held at a constant temperature of approximately 38° C. Sensor calibration information may be determined from this comparison to the temperature standard and stored in a calibration integrated circuit attached permanently to each individual sensor (in the connector housing).

Once calibrated, the arrays may be tested in experiments to assess their ability to record temperatures of a surface accurately without self-heating in high intensity microwave or ultrasound fields or perturbing ultrasound or microwave applicator power deposition patterns. In an initial prototype test, the thermal barrier properties were characterized for a 0.28 mm thick Kapton array with sixteen 250 μm diameter sensors (TMS-250) with the array placed between a large uniform temperature surface (well-circulated water bolus) and an air insulated thermal load.

Eight 0.64 mm OD Teflon encased multi-sensor thermocouples were placed above, and another eight thermocouples placed below the TMS-250 sheet in good thermal contact with the water bolus, Kapton sheet, and air bladder insulation layers to monitor interface temperatures. After circulating 23° C. water until steady state conditions were obtained, the tubing connections were switched to a preheated bath at time t=100 s and the water bolus increased rapidly towards 40.5° C. Sensors on opposing sides of the 0.28 mm Kapton sandwich registered different temperatures due to thermal resistance of the thin barrier. The temperature difference on either side of the TMS was, in this example test, about 2° C. initially reducing to just over 1° C. in steady state, as measured by the thinwall Teflon encased thermocouples.

Another test of the effect on microwave array heating patterns of a complete TMS array may be conducted, for example, using a 6-element sub-array of a large CMA applicator that has been used for treating large area chestwall disease. Insertion of the 0.28 mm thick thermal monitoring sheet with 250 μm fibers has essentially no effect on the radiated field from the microwave array other than to reduce the peak SAR at a depth of 5 mm in muscle by about 5%. Since a separate investigation demonstrated no absorption of microwave energy directly in the Kapton based sensor array, this minor reduction in transmitted power must have been due to slight changes in driving impedance and/or slight reflections at the additional dielectric interface (adding to reflections already occurring from the waterbolus PVC dielectric interface). That minor effect would easily be accommodated in clinical treatments by increasing the applied power, as necessary to achieve the desired skin surface temperature.

Additionally, the following observations and conclusions can be ascertained from the characterization of the TMS devices:

Thin (0.1-0.3 mm, typical) and flexible thermal monitoring sheet arrays can be constructed from readily available and easily manufactured dielectric sheets (e.g. Kapton) which support an array of 250-500 μm diameter (typical) plastic fibers;

0.1-0.3 mm Kapton TMS have no perceptible absorption or self-heating from 915 MHz microwave energy;

0.1-0.3 mm Kapton TMS with 250-500 μm fibers placed between microwave array applicator and tissue load produces no perceptible change in SAR pattern, and ≦5% reduction in peak SAR;

0.1-0.3 mm Kapton TMS has minimal absorption and perturbation of 3.4 MHz ultrasound energy, with self-heating of ≦1-2° C. across the array surface for typical applied power levels;

Kapton TMS fiber-optic arrays ≦0.3 mm thick offer a simple and accurate way to monitor surface temperature distributions, producing transient offsets <0.5° C. even up to three times the typical clinical temperature gradient; and TMS arrays should provide improved monitoring of temperature distributions in large surface areas due to fast simultaneous reading of multiple temperatures, consistent thermal resistance between sensors and surface to be measured, and fixed known location of all sensors in the array.

Although the invention has been described with respect to various embodiments, it should be realized this invention is also capable of a wide variety of further and other embodiments within the spirit and scope of the appended claims.

What is claimed is:

1. A thermal monitoring device comprising:
a first plurality of conduits for conveying electromagnetic radiation in a first predetermined direction;
a second plurality of conduits for conveying electromagnetic radiation in a second predetermined direction, said second plurality of conduits intersecting said first plurality of conduits at a plurality of intersecting positions;
a plurality of temperature sensing components, with a separate temperature sensing component located at each of the intersecting positions;
a flexible component maintaining said first and said second plurality of conduits in a fixed relative arrangement with respect to each other;
each of said first plurality of conduits having a portion that terminates in a first connector; and
each of said second plurality of conduits having a portion that terminates in a second connector;
wherein electromagnetic radiation can be input through said first connector via said first plurality of conduits to each said temperature sensing component, each said temperature sensing component providing an output through said second connector indicative of temperature substantially at said temperature sensing component.

2. The thermal monitoring device of claim 1 wherein said flexible component comprises dielectric sheet material.

3. The thermal monitoring device of claim 1 wherein at least one of said conduits comprises an optical waveguide; and
at least one of said first connector and said second connector comprises a multi-terminal optical connector.

4. The thermal monitoring device of claim 1 wherein at least one said separate temperature sensing component comprises a phosphor with temperature-dependent fluorescence decay.

5. The thermal monitoring device of claim 4 wherein said electromagnetic radiation comprises light.

6. The thermal monitoring device of claim 1 further comprising:
a third connector and a fourth connector;
said third connector and said fourth connector comprising a plurality of interface conduits; and
at least one of said interface conduits terminating at another connector.

7. The thermal monitoring device of claim 6 wherein said another connector accesses electronic means for activating and interfacing with each of said separate temperature sensing components in order to provide temperature readings at sites of each said separate temperature sensing component.

8. The thermal monitoring device of claim 7 wherein at least one of said third connector and fourth connector is detachable from said first connector and said second connector, respectively.

9. A thermal monitoring device comprising:
a first plurality of conduits for conveying electromagnetic radiation in a first predetermined direction;
a second plurality of conduits for conveying electromagnetic radiation in a second predetermined direction, said second plurality of conduits intersecting said first plurality of conduits at a plurality of intersecting positions;
a plurality of temperature sensing components, with a separate temperature sensing component located at each of the intersecting positions;
a flexible component maintaining said first and said second plurality of conduits in a fixed relative arrangement with respect to each other;
electronic means for activating and interfacing with each said separate temperature sensing component; and
said electronic means includes means for directing the electromagnetic radiation into at least one conduit of said first plurality of conduits in order to activate said temperature sensing components located along the at least one conduit, and means for accessing the outputs from said temperature sensing components located along the one conduit through said second plurality of conduits in order to determine temperature at various locations of the temperature sensing components along the one conduit.

10. The thermal monitoring device of claim 9 wherein said flexible component comprises dielectric sheet material.

11. The thermal monitoring device of claim 9 wherein at least one of said conduits comprises an optical waveguide.

12. The thermal monitoring device of claim 9 wherein at least one said separate temperature sensing component comprises a phosphor with temperature-dependent fluorescence decay.

13. The thermal monitoring device of claim 9 wherein said electromagnetic radiation comprises light.

14. A method of sensing temperature at a plurality of locations, comprising the steps of:
providing a first plurality of conduits for conveying electromagnetic radiation in a first predetermined direction;
providing a second plurality of conduits for conveying electromagnetic radiation in a second predetermined direction, said second plurality of conduits intersecting said first plurality of conduits at a plurality of intersecting positions;
providing separate temperature sensing components, each temperature sensing component located at one of the intersecting positions;
maintaining said first and said second plurality of conduits in a fixed relative arrangement with respect to each other;
directing electromagnetic radiation into one conduit of said first plurality of conduits in order to activate the temperature sensing components located along the one conduit; and
accessing outputs from the temperature sensing components located along the one conduit through the second plurality of conduits in order to determine temperature at various of the temperature sensing components along the one conduit.

15. The temperature sensing method of claim 14 further comprising the steps of:
sequentially directing electromagnetic radiation into other conduits of said first plurality of conduits in order to activate the temperature sensing components located along the other conduits; and
accessing the outputs from the temperature sensing components located along the other conduits through the second plurality of conduits in order to determine temperature at various of the temperature sensing components along the other conduits.

16. The method of sensing temperature at a plurality of locations as defined in claim 14 wherein said step of maintaining fixed relative position of the temperature sensing components comprises the use of a dielectric sheet material.

17. The method of sensing temperature at a plurality of locations as defined in claim 16 wherein at least one of said conduits comprises an optical waveguide.

18. The method of sensing temperature at a plurality of locations as defined in claim 17 wherein at least one said separate temperature sensing component comprises a phosphor with temperature-dependent fluorescence decay.

19. The method of sensing temperature at a plurality of locations as defined in claim 18 wherein said electromagnetic radiation comprises light.

20. A thermal monitoring device comprising:
a plurality of waveguides for conveying electromagnetic radiation in a series of predetermined directions;
a plurality of temperature sensing components, with a separate temperature sensing component located at each of said plurality of conduits;
a flexible component maintaining said conduits in a fixed relative arrangement with respect to each other;
each of said plurality of conduits having a portion that terminates in a first connector; and a second connector removably affixed to said first connector;
wherein electromagnetic radiation can be input through said second connector via said first connector to said plurality of conduits to each said temperature sensing component, each said temperature sensing component providing an output indicative of temperature.

21. The thermal monitoring device of claim 20 wherein at least one said separate temperature sensing component comprises a phosphor with temperature-dependent fluorescence decay.

22. The thermal monitoring device of claim 21 wherein said electromagnetic radiation comprises light.

* * * * *

UNITED STATES PATENT AND TRADEMARK OFFICE
CERTIFICATE OF CORRECTION

PATENT NO.         : 8,075,181 B1
APPLICATION NO.    : 12/475151
DATED              : December 13, 2011
INVENTOR(S)        : Paul Rath Stauffer et al.

Page 1 of 1

It is certified that error appears in the above-identified patent and that said Letters Patent is hereby corrected as shown below:

On the Title page, Item (73) Assignee, "The Regents of the University of California, Oakland, CA (US)" should read -- The Regents of the University of California, Oakland, CA (US) and IPICOM, Inc., Carlsbad, CA (US) --

Signed and Sealed this
Fifth Day of June, 2012

David J. Kappos
*Director of the United States Patent and Trademark Office*